(12) United States Patent
Bui et al.

(10) Patent No.: US 8,540,973 B2
(45) Date of Patent: *Sep. 24, 2013

(54) REFRESHING CREAM FOUNDATION IN GEL FORM

(75) Inventors: Hy Si Bui, Piscataway, NJ (US);
Mohamed Kanji, Edison, NJ (US);
Chunhua Li, Scotch Plains, NJ (US);
Anita Chon Tong, Westfield, NJ (US);
Bruno Bavouzet, Hoboken, NJ (US);
Susan Halpern, Paramus, NJ (US)

(73) Assignee: L'Oréal, Paris (FR)

( * ) Notice: Subject to any disclaimer, the term of this patent is extended or adjusted under 35 U.S.C. 154(b) by 6 days.

This patent is subject to a terminal disclaimer.

(21) Appl. No.: 12/825,730

(22) Filed: Jun. 29, 2010

(65) Prior Publication Data

US 2011/0020254 A1    Jan. 27, 2011

Related U.S. Application Data

(60) Provisional application No. 61/221,377, filed on Jun. 29, 2009, provisional application No. 61/221,295, filed on Jun. 29, 2009.

(51) Int. Cl.
*A61K 8/00* (2006.01)
*A61K 8/18* (2006.01)
*A61K 31/74* (2006.01)
*A61Q 1/02* (2006.01)
*A61Q 19/04* (2006.01)

(52) U.S. Cl.
USPC .......................................... 424/63; 424/78.03

(58) Field of Classification Search
USPC ................................................ 424/63, 78.03
See application file for complete search history.

(56) References Cited

U.S. PATENT DOCUMENTS

| 5,998,547 | A  | * | 12/1999 | Hohner | 525/301 |
|-----------|----|----|---------|--------|---------|
| 6,482,400 | B1 | * | 11/2002 | Collin | 424/70.6 |
| 2004/0223986 | A9 | * | 11/2004 | Boussouira et al. | 424/401 |
| 2007/0031361 | A1 | * | 2/2007 | Herrmann et al. | 424/70.11 |
| 2007/0110702 | A1 | * | 5/2007 | Ehara | 424/70.31 |
| 2008/0207871 | A1 |   | 8/2008 | Seiler et al. | |

FOREIGN PATENT DOCUMENTS

| EP | 2 036 536 |   | 3/2009 |
|----|-----------|---|--------|
| WO | WO 96/03967 |   | 2/1996 |
| WO | WO 01/17485 | * | 3/2001 |
| WO | WO 2006/112690 |   | 10/2006 |
| WO | WO 2007/048672 | * | 3/2007 |
| WO | WO 2007/096400 | * | 8/2007 |
| WO | WO 2008/046763 | * | 4/2008 |

OTHER PUBLICATIONS

Hauthal, Tenside Surf. Det. 2008, 45(1), 30-42.*
U.S. Appl. No. 12/825,707, filed Jun. 29, 2010, Bui, et al.
U.S. Appl. No. 12/825,767, filed Jun. 29, 2010, Bui, et al.
U.S. Appl. No. 12/825,807, filed Jun. 29, 2010, Bui, et al.
U.S. Appl. No. 12/825,587, filed Jun. 29, 2010, Bui, et al.
U.S. Appl. No. 12/825,840, filed Jun. 29, 2010, Bui, et al.
U.S. Appl. No. 12/825,623, filed Jun. 29, 2010, Bui, et al.
U.S. Appl. No. 12/825,726, filed Jun. 29, 2010, Bui, et al.
U.S. Appl. No. 12/825,633, filed Jun. 29, 2010, Bui, et al.
U.S. Appl. No. 12/825,599, filed Jun. 29, 2010, Bui, et al.
U.S. Appl. No. 12/825,816, filed Jun. 29, 2010, Bui, et al.
U.S. Appl. No. 12/825,614, filed Jun. 29, 2010, Bui, et al.
U.S. Appl. No. 12/825,600, filed Jun. 29, 2010, Bui, et al.
U.S. Appl. No. 12/825,559, filed Jun. 29, 2010, Bui, et al.
U.S. Appl. No. 13/133,176, filed Jun. 7, 2011, Bui, et al.
U.S. Appl. No. 13/133,181, filed Aug. 1, 2011, Bui, et al.
U.S. Appl. No. 13/379,691, filed Dec. 21, 2011, Bui, et al.
European Search Report issued Apr. 6, 2011, in European Patent Application No. 10167794.6.

* cited by examiner

*Primary Examiner* — Fereydoun G Sajjadi
*Assistant Examiner* — Genevieve S Alley
(74) *Attorney, Agent, or Firm* — Oblon, Spivak, McClelland, Maier & Neustadt, L.L.P.

(57) ABSTRACT

The present invention is directed to a cosmetic composition includes (a) at least one polyamine; (b) at least one oil-soluble polar modified polymer; (c) at least one gelling agent; (d) at least one hyperbranched polyol; and (e) water.

28 Claims, No Drawings

REFRESHING CREAM FOUNDATION IN GEL FORM

CROSS-REFERENCE TO RELATED APPLICATIONS

This application claims the benefit of priority from U.S. Provisional Application Ser. Nos. 61/221,295 and 61/221,377, both filed Jun. 29, 2009, the entire contents of which are hereby incorporated by reference.

FIELD OF THE INVENTION

The present invention generally relates to a novel composition which is hydrating and refreshing in cream form, which also has excellent long wearing properties.

BACKGROUND OF THE INVENTION

Many compositions, especially cosmetic compositions, have been developed for easy and comfortable application onto a targeted substrate. Unfortunately, many of these compositions are in fact difficult to apply and do not possess a smooth feel upon application. Moreover, compositions often have a tendency to feel tacky, yielding poor application and spreadability characteristics. Similarly, the use of silicone resins to impart transfer resistance onto a colored cosmetic product suffers from the same disadvantages disclosed above.

Therefore, it is desirable to provide a composition capable of possessing a creamy texture and feel with highly moisturizing and long wearing properties without the need for having to use expensive ingredients and/or processing techniques.

BRIEF SUMMARY OF THE INVENTION

A first aspect of the present invention is directed to a composition that includes: (a) at least one polyamine; (b) at least one oil-soluble polar modified polymer; (c) at least one hyperbranched polyol; (d) at least one gelling agent; and (e) water.

The present invention also relates to compositions which include: (a) a reaction product of at least one polyamine and/or hyperbranched polyol with at least one oil-soluble polar modified polymer; (b) at least one gelling agent; and (c) water.

The present invention also relates to a composition made by combining: (a) at least one polyamine; (b) at least one oil-soluble polar modified polymer; (c) at least one hyperbranched polyol; (d) at least one gelling agent; and (e) water.

A second aspect of the present invention is directed to a method of making up a keratinous substrate comprising applying the above-disclosed composition onto the substrate.

It has been surprisingly discovered that this composition displays a high amount of moisturization to the keratinous substrate and is longwearing in the absence of silicone resins and traditional film formers. Further, the composition provides a unique texture and is stable.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Keratinous substrates", as used herein, include but are not limited to, skin, lips, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25 C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 400 C., 450 C., 500 C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C. "Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions.

Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA." "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMace copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemcial Co., poly(ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil soluble polar modified polymer(s) represent from about 1% to about 30% of the total weight of the composition, more preferably from about 2.5% to about 15% of the total weight of the composition, and most preferably from about 5% to about 10%, including all ranges and subranges therebetween.

Hyperbranched Polyol Compound

According to the present invention, compositions comprising at least one hyperbranched polyol compound are provided. In accordance with the present invention, the hyperbranched polyol compound has at least two hydroxyl groups available to react with hydrophilic groups on the backbone of the polar modified wax.

"Hydroxyl number" or "hydroxyl value" which is sometimes also referred to as "acetyl value" is a number which indicates the extent to which a substance may be acetylated; it is the number of milligrams of potassium hydroxide required for neutralization of the acetic acid liberated on saponifying 1 g of acetylated sample. According to preferred embodiments, the at least one hyperbranched polyol has a hydroxyl number between 50 and 250, preferably between 75 and 225, preferably between 100 and 200, preferably between 125 and 175, including all ranges and subranges therebetween such as 90 to 150.

In accordance with the present invention, "hyperbranched polyol" refers to dendrimers, hyperbranched macromolecules and other dendron-based architectures. Hyperbranched polyols can generally be described as three-dimensional highly branched molecules having a tree-like structure. They are characterized by a great number of end groups, at least two of which are hydroxyl groups. The dendritic or "tree-like" structure preferably shows regular symmetric branching from a central multifunctional core molecule leading to a compact globular or quasi-globular structure with a large number of end groups per molecule. Suitable examples of hyperbranched polyols can be found in U.S. Pat. No. 7,423, 104, and U.S. patent applications 2008/0207871 and 2008/0286152, the entire contents of all of which are hereby incorporated by reference. Other suitable examples include alcohol functional olefinic polymers such as those available from New Phase Technologies.

Dendrimers tend to be exact, monodisperse structures built layerwise (in generations) around a core moiety, with a polymer branching point in every repeating unit. Hyperbranched polymers tend to possess a number of characteristics which are similar to dendrimers but they tend to be polydispersed and contain relatively linear segments off of which a plurality of highly branched segments are grown or attached.

Furthermore, "hyperbranched polymers" refers to polymers comprising at least two, for example three, polymeric branches, forming either the main branch or a secondary branch, and each comprising at least one at least trifunctional branch point, which may be identical or different, and which is able to form at least two at least trifunctional branch points, different from and independent of one another. Each branch point may be, for example, arranged in the interior of at least one chain. The branches may be, for example, connected to one another by a polyfunctional compound.

As used herein, "trifunctional branch point" means the junction point between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least trifunctional branch" means the junction points between at least three polymeric branches, for example n polymeric branches, of which n−1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

According to particularly preferred embodiments of the present invention, the hyperbranched polyol comprises a hydrophobic chain interior. Preferably, the chain interior comprises one or more hydrocarbon groups, one or more silicon-based groups, or mixtures thereof. Particularly preferred chain interiors comprise olefinic polymers or copolymers and/or silicone polymers or copolymers.

Suitable olefinic monomers include, but are not limited to, compounds having from about 2 to about 30 carbon atoms per molecule and having at least one olefinic double bond which are acyclic, cyclic, polycyclic, terminal α, internal, linear, branched, substituted, unsubstituted, functionalized, and/or non-functionalized. For example, suitable monomers include ethylene, propylene, 1-butene, 2-butene, 3-methyl-1-butene, and isobutylene.

Suitable silicone groups for inclusion into the interior chain include "D" groups (for example, dimethicone or substituted dimethicone groups).

An exemplary structure is as follows:

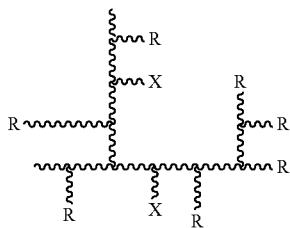

An exemplary structure Where X corresponds to hydroxyl functionality and R corresponds to a methyl group or an alkyl group preferably containing 2-30 atoms.

According to preferred embodiments, the at least one hyperbranched polyol has a molecular weight (Mw) between about 3,000 and 25,000, preferably between 4,000 and 22,000, preferably between 5,000 and 20,000, including all ranges and subranges therebetween such as 4000 to 5500.

According to preferred embodiments, the at least one hyperbranched polyol has a viscosity at 90° F. of between 1,000 and 8,000 centipoise (cps), preferably 2,000 and 7,000 cps, and preferably 3,000 and 6,000 cps, including all ranges and subranges therebetween.

According to preferred embodiments, the at least one hyperbranched polyol is present in the composition of the present invention in an amount ranging from about 0.1 to about 15% by weight, more preferably from about 1 to about 10% by weight, most preferably from about 2 to about 8% by weight, based on the total weight of the composition, including all ranges and subranges within these ranges.

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-05 polyalkyleneamine compound, more preferably a polyethyleneimine or polypropyleneimine. Most preferably, the polyalkylenamine is polyethyleneimine ("PEI"). The polyalkylenamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. No. 5,530,092 and U.S. Pat. No. 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polymamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.05 to about 20% by weight, more preferably from about 0.2 to about 10% by weight, more preferably from about 0.5 to about 5% by weight, based on the total weight of the composition, including all ranges and subranges within these ranges.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified ratio is between 0.005 and 1, preferably between 0.006 and 0.5, and preferably between 0.007 and 0.1, including all ranges and subranges therebetween.

Gelling Agent

According to the present invention, compositions comprising at least one gelling agent chosen from cellulose, and derivates thereof are provided. Such gelling agents are typically found in the aqueous phase of a composition.

Examples of suitable cellulose, and derivatives thereof include, but are not limited to:

cellulose polymers such as hydroxyethylcellulose, hydroxypropylcellulose, methylcellulose, ethylhydroxyethylcellulose, carboxymethylcellulose, and quaternized cellulose derivatives;

cellulosic thickeners, for example, hydroxyethylcellulose, hydroxypropylcellulose, and carboxymethylcellulose, guar gum and its derivatives, such as hydroxypropylguar, gums of microbial origin, such as xanthan gum and scleroglucan gum;

quaternized cellulose derivatives and polyacrylates containing non-cyclic amine side groups. The quaternized cellulose derivatives may include, for example:

quaternized celluloses modified with groups comprising at least one fatty chain, such as alkyl, arylalkyl, and alkylaryl groups comprising at least 8 carbon atoms, and mixtures thereof;

quaternized hydroxyethylcelluloses modified with groups comprising at least one fatty chain, such as alkyl, arylalkyl, and alkylaryl groups comprising at least 8 carbon atoms, and mixtures thereof;

polyquaternium-37 (commercially available from Cognis under the trademark name Ultragel 300 and from Ciba under the trademark name SalCARE); hydroxyalkyl cellulose polymers and alkyl hydroxyalkyl cellulose polymers such as hydroxyethyl cellulose (commercially available from Amerchol and The Dow Chemical Company and Hercules under the tradenames Cellosize and Natrosol), hydroxypropyl cellulose (commercially available from Hercules under the tradename Klucel) and cetyl hydroxyethyl cellulose (commercially available from Hercules under the tradename Natrosol);

carboxymethyl cellulose (commercially available from Hercules under the tradename Aqualon), natural or synthetic gums, and starches;

quaternized alkylhydroxyethylcelluloses containing C8-C30 fatty chains include, for instance, the products Quatrisoft LM 200, Quatrisoft LM-X 529-18-A, Quatrisoft LM-X 529-18B (C12 alkyl), and Quatrisoft LM-X 529-8 (C18 alkyl) sold by the company Amerchol, and the products Crodacel QM, Crodacel QL (C12 alkyl) and Crodacel QS (C18 alkyl) sold by the company Croda.

Particularly preferred thickening agents are polysaccharides or polysaccharide derivatives such as hydroxyethyl cellulose, hydroxypropyl cellulose, methyl cellulose, xanthan gum, guar gum, hydroxymethylcellulose derivatives such as hydroxypropyl methylcellulose and hydroxybutyl methyl cellulose, starch and starch derivatives.

Particularly preferred rheology-modifying agents are cetyl hydroxyethyl cellulose, quaternized celluloses and hydroxyethylcelluloses.

Preferably, the gelling agent is present in the composition of the present invention in an amount ranging from about 0.1% to about 10.0% by weight, preferably from about 0.5% to about 5.0% by weight, preferably from about 1.0% to about 4.0% by weight of the total weight of the composition, including all ranges and subranges therebetween.

Reaction Product

According to preferred embodiments of the present invention, the oil-soluble polar modified polymer is reacted with the polyamine compound, in the presence of water in, at minimum, an amount sufficient to solubilize the polyamine, to form a reaction product. In accordance with the preferred embodiments, the reaction product is water-insoluble.

Although not wanting to be bound by any particular theory, it is believed that at a temperature below 100° C., the reaction of the oil-soluble polar modified polymer with the primary amine group of the polyamine opens the anhydride ring to form a half acid and half amide crosslinked product. However, at a temperature above 100° C., the reaction of the oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the oil-soluble polar modified polymer is in an oil carrier, and the polyamine compound is in an aqueous carrier, and the reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof. Moreover, the product is both stable and capable of carrying various types of ingredients.

Similarly, according to preferred embodiments of the present invention, the reaction of the oil-soluble polar modified polymer and polyol in an anhydrous system (oil phase only) can create a reaction product. Without intending to be bound by any particular theory, it is believe that the reaction product of the oil-soluble polar modified polymer and the hyperbranched polyol is an elastomer-type compound having ester linkages which can swell in polar solvents or can disperse into the water phase.

Water

The composition of the present invention also contains water. The water is typically present in an amount of from about 5% to about 50% by weight, such as from about 10% to about 40% by weight, such as from about 25% to about 35% by weight, including all ranges and subranges therebetween, all weights being based on the total weight of the composition. According to particularly preferred embodiments, sufficient water is present to form a water-in-oil emulsion.

Optional Ingredients

Gelling Agent

It may be desirable to employ an additional gelling agent, other than cellulose and derivatives thereof. Examples of such other gelling agents include:

water-soluble gelling polymers such as:

proteins, such as proteins of plant origin, for instance wheat proteins and soy proteins; proteins of animal origin such as keratins, for example keratin hydrolysates and sulphonic keratins;

anionic, cationic, amphoteric or nonionic chitin or chitosan polymers; and synthetic thickeners such as crosslinked homopolymers of acrylic acid and of acrylamidopropanesulphonic acid;

fatty acid amides such as coconut diethanolamide and monoethanolamide, and oxyethylenated monoethanolamide of carboxylic acid alkyl ether, and associative polymers.

Cationic associative polymers may include, but are not limited to:

cationic associative polyurethanes which may be formed from diisocyanates and from various compounds with functions containing a labile hydrogen. The functions containing a labile hydrogen may be chosen from alcohol, primary and secondary amine, and thiol functions, giving, after reaction with the diisocyanate functions, polyurethanes, polyureas, and polythioureas, respectively. The expression "polyurethanes which can be used according to the present invention" encompasses these three types of polymer, namely polyurethanes per se, polyureas and polythioureas, and also copolymers thereof. Example of such compounds include, but are not limited to, methylenediphenyl diisocyanate, methylenecyclohexane diisocyanate, isophorone diisocyanate, tolylene diisocyanate, naphthalene diisocyanate, butane diisocyanate, and hexane diisocyanate; and carboxyvinyl polymers, acrylic acid/polyallyl sucrose copolymers, polyacrylic compounds and acrylic acid/ethyl acrylate copolymers (commercially available under the CARBOPOL tradenames).

If present, such other gelling agent is preferably present in the composition of the present invention in an amount ranging from about 0.1% to about 10.0% by weight, preferably from about 0.5% to about 5.0% by weight, preferably from about 1.0% to about 4.0% by weight of the total weight of the composition.

Volatile Solvent Other than Water

The cosmetic composition of the present invention can comprise at least one volatile solvent. In an embodiment of the present invention, the at least one volatile solvent may be chosen from a volatile silicone oil or a volatile non-silicone oil.

Suitable volatile silicone oils include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5cSt) from Dow Corning | 56 | 1.5 |
| PDMS DC 200 (2cSt) from Dow Corning | 87 | 2 |
| PDMS DC 200 (3St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, isohexadecane, and for example, the oils sold under the trade names of Isopar or Permethyl, the C8 to C16 branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

If present, the at least one volatile solvent is present in the composition in an amount of from about 20 to about 90% by weight, such as from about 30 to about 80% by weight, and from about 35 to about 75% by weight, all weights based on the total weight of the composition, including all ranges and subranges therebetween.

Non-Volatile Solvent for Oil-Soluble Polar Modified Polymer

The cosmetic composition of the present invention can comprise at least one non-volatile oil capable of dissolving the oil-soluble polar modified polymer. As used herein, the term "non-volatile" means having a boiling point of greater than about 100 degrees C.

Examples of non-volatile oils that may be used in the present invention include, but are not limited to, polar oils such as:

- hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;
- synthetic oils or esters of formula R5COOR6 in which R5 represents a linear or branched higher fatty acid residue containing from 1 to 40 carbon atoms, including from 7 to 19 carbon atoms, and R6 represents a branched hydrocarbon-based chain containing from 1 to 40 carbon atoms, including from 3 to 20 carbon atoms, with R6+R7≥10, such as, for example, Purcellin oil (cetostearyl octanoate), isononyl isononanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
- synthetic ethers containing from 10 to 40 carbon atoms;
- C8 to C26 fatty alcohols, for instance oleyl alcohol; and mixtures thereof.

Further, examples of hydrocarbon oils which may be used include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

If present, the at least one non-volatile solvent is preferably present in the composition of the invention in an amount of from about 1% to about 20% by weight, such as from about 1.5% to about 10% by weight, such as from about 2% to about 5% by weight, all weights based on the total weight of the composition.

The composition of the present invention may also include other ingredients. Examples thereof include, but are not limited to, colorants such as dyes and pigments, co-solvents (volatile and/or non-volatile), waxes, plasticizers, preservatives, fillers, active ingredients such as those used to treat skin and hair and sunscreens.

It has surprisingly been discovered that the composition of the present invention is highly transfer resistant and long wearing, and in order to be effective as a base/matrix for carrying insoluble ingredients, does not require the use of silicone resins, emulsifiers or gelling agents. The resulting is also able to provide a composition capable of possessing a gel texture and nice feel with highly moisturizing and long wearing properties without the need for having to use expensive ingredients and/or processing techniques The composition of the present invention may be used for any application in which it is desirable to employ a waterproof film, capable of carrying insoluble ingredients such as, for example, pigments, and which is stable, easily spreadable, and comfortable to apply.

The present invention is further described in terms of the following non-limiting examples. Unless otherwise indicated, all parts and percentages are on a weight-by-weight percentage basis.

Example 1

Lip Stick Composition

| Phase | Chemical Name | Ex 1 |
| --- | --- | --- |
| A | Polyglyceryl-2 Triisosterate | 3.00 |
| A | Octyldodecyl Neopantanoate | 15.23 |
| A | Hydrogenated Polydecene | 15.23 |
| A | Hyperbranched polyol | 5.00 |
| A | Polyethylene 400 | 8.00 |
| A | Polypropylene-ethylene-maleic anhydride copolymer wax | 7.00 |
| A | Color Pigments | 5.00 |
| A | Tricaprylin | 13.80 |
| A | Mica | 2.00 |
| B | Deionized Water | 22.50 |
| B | Glycerin | 3.00 |
| B | PEI-35 | 0.25 |

Procedure

The following were added to a suitable size beaker A and heated to 95 Celsius degrees: Polyglyceryl-2 Triisosterate, octyldodecyl neopantanoate, hydrogenated polydecene, Hyperbranched polyol, polyethylene 400, Polypropylene-ethylene-maleic anhydride copolymer wax.

When enough solids had melted, the contents were mixed with moderate speed until all solids had melted at 95 Celsius degrees.

The temperature was slightly lowered to 85 Celsius degrees and pigments, tricaprylin and mica were added.

The contents of main beaker A was transferred to a Silverson mixer for emulsification while maintaining the temperature at 85-90 Celsius degrees.

In a separate beaker 2, glycerin and PEI-35 were added into DI water and mixed and heated to 85 Celsius degrees.

The contents of side beaker B was added dropwise into the beaker A while emulsifying at 9000 rpm under the Silverson mixer for 30 minutes.

Afterward, the emulsification speed was lowered to 2000 rpm for 5 minutes.

The contents were poured into lipstick molds at 80 Celsius degrees.

The lipstick in molds was placed in a cooling tunnel for 15 minutes at −10 Celsius degrees. Once cooled, the lipstick in molds were removed from the cooling tunnel to equilibrate to 25 Celsius degrees and removed from mold after lipsticks had thawed to 25 Celsius degrees.

Example 2

Lip Gloss Composition

| Phase | Chemical Name | Ex 2 |
|---|---|---|
| A | Polyglyceryl-2 Triisosterate | 6.00 |
| A | Octyldodecyl Neopantanoate | 8.95 |
| A | Hydrogenated Polydecene | 8.95 |
| A | Hyperbranched polyol | 5.00 |
| A | Polypropylene-ethylene-maleic anhydride copolymer wax | 7.00 |
| A | Color Pigments | 5.00 |
| A | Tricaprylin | 13.80 |
| A | Mica | 2.00 |
| B | Deionized Water | 40.00 |
| B | Glycerin | 3.00 |
| B | PEI-35 | 0.25 |

The following were added to a suitable size beaker A and heated to 95 Celsius degrees: Polyglyceryl-2 Triisosterate, octyldodecyl neopantanoate, hydrogenated polydecene, Hyperbranched polyol, Polypropylene-ethylene-maleic anhydride copolymer wax.

When enough solids had melted, the contents were mixed with moderate speed until all solids had melted at 95 Celsius degrees.

The temperature was slightly lowered to 85 Celsius degrees and pigments, tricaprylin and mica were added.

The contents of main beaker A was transferred to a Silverson mixer for emulsification while maintaining the temperature at 85-90 Celsius degrees.

In a separate beaker 2, glycerin and PEI-35 were added into DI water and mixed and heated to 85 Celsius degrees.

The contents of side beaker B was added dropwise into the beaker A while emulsifying at 9000 rpm under the Silverson mixer for 30 minutes.

Afterward, the emulsification speed was lowered to 2000 rpm for 5 minutes and was cooled to 25 Celsius degrees.

The contents of main beaker A was poured into container.

Example 3

Mascara Composition

Step One: Make the PPMA-PEI Gel

| Phase | Component | Example1 Gel |
|---|---|---|
| A | Caprylic/capric Triglyceride | 1 |
| A | Polylene ethylene Maleic Anhydride Copolymer | 9.33 |
| A | Iron Oxides | 8 |
| A | Isododecane | 39.92 |
| A | Propylparaben | 0.2 |
| B | DI Water | 34 |
| B | Disodium EDTA | 0.1 |
| B | Potassium Cetyl Phosphate | 2 |
| B | Methylparaben | 0.25 |
| B | Pentylene Glycol | 2 |
| B | PEI-35 | 2 |
| C | Simethicone | 0.1 |
| D | Phenoxyethanol (and) Methylparaben (and) Isopropylparaben (and) Isobutylparaben (and) Butylparaben | 1.1 |
| | Total | 100 |

Procedures

In the main beaker A, add Isododecane, Caprylic/capric Triglyceride, Polylene ethylene Maleic Anhydride Copolymer, Propylparaben. Heat the content to 90° C. until all solids have melted.

Add Iron Oxides into main beaker and start homogenizing batch for 1 h at 850 RPM. (Temperature maintained at 85-90° C.)

In a side beaker B, add ID water, Disodium EDTA, Potassium Cetyl Phosphate, Methylparaben, Pentylene Glycol. Mix until uniform. Heat content to 90° C.

In the side beaker B, Add PEI, Mix until PEI dissolved. (Temperature maintained at 85-90° C.)

Slowly add side beaker B to main beaker A. Then add Simethicone to the mixture. The gel formation was observed in 5 minutes after mixing A and B.

During the gel formation, slow down the mixing speed from 250 RPM to 100 RPM to 50 RPM.

Once the gel network became thick enough, change to sweep blade. Start cooling using 50 RPM.

At 35° C., add the mixture of Phenoxyethanol (and) Methylparaben (and) Isopropylparaben (and) Isobutylparaben (and) Butylparaben.

Continue cooling to 25° C. and drop batch at 25° C.

Step Two: Blend Polyol with PPMA-PEI Gel

| Phase | Component | Example1 |
|---|---|---|
| A | PPMA-PEI Gel | 90 |
| A | Hyperbranched Polyalpha Olefins | 10 |
| | Total | 100 |

Procedure:

Heated the Hyperbranched Polyalpha Olefins to 40° C. Blended the PPMA-PEI gel with Hyperbranched Polyalpha Olefins according to 9:1 ratio under 200 RPM for 20 mins.

Example 4

A cosmetic composition was prepared containing the below-disclosed ingredients.

| isohexadecane | 2.25 |
|---|---|
| isododecane | 40.15 |
| PP207 * | 6.75 |
| polyglyceryl-2 triisostearate | 2.50 |
| DI Water | 25.50 |
| cellulose | 0.20 |

| | |
|---|---|
| Hyperbranched polyol | 10.00 |
| Polyethyleneimine | 0.75 |
| TITANIUM DIOXIDE | 7.82 |
| IRON OXIDES | 1.46 |
| IRON OXIDES | 0.52 |
| IRON OXIDES | 0.20 |
| DISODIUM EDTA | 0.20 |
| propylene glycol | 0.50 |
| PHENOXY-2 ETHANOL | 0.80 |
| CHLORPHENESIN | 0.20 |
| ETHYL PARABEN | 0.20 |
| TOTAL | 100.00 |

(*) PP207 is a linear polypropylene-ethylene-maleic anhydride copolymer wax commercially available from Clariant under the tradename LICOCARE PP207 LP 3349.

Procedure

In container A, PP207 was melted in the isohexadecane and isododecane until fully dissolved. The temperature was brought to 900 C.

While maintaining the temperature, the hyperbranched polyol, emulsifier and pigment grind were added to container A until fully dissolved.

In separate container B, water, Polyethyleneimine, cellulose, and preservatives were mixed at 90 C B was added to A slowly at high sheer (~700 rpm).

Heat was maintained at 700 C-800 C for 20 minutes while maintaining high sheer mixing.

The mixture was cooled to room temperature while mixing.

What is claimed is:

1. A composition comprising:
   a water-insoluble, half acid and half amide crosslinked reaction product comprising (1) at least one oil-soluble polar modified polymer comprising at least one C2-C4 monomer and modified with at least one hydrophilic unit, and having a weight-average molecular weight of less than or equal to 25,000 g/mol and a melting point above 75° C. and (2) at least one polyamine, wherein the reaction product forms a matrix capable of entrapping water;
   at least one gelling agent;
   at least one hyperbranched polyol; and
   water,
   wherein the composition is in the form of an emulsion and wherein water is entrapped within the matrix.

2. The composition of claim 1, further comprising at least one volatile oil.

3. The composition of claim 1, further comprising at least one non-volatile oil.

4. The composition of claim 1, wherein the at least one polyamine is a branched polyalkyleneimine.

5. The composition of claim 1, wherein the polyamine is present in an amount of from about 0.05 to about 20% by weight, based on the weight of the composition.

6. The composition of claim 4, wherein the polyamine is present in an amount of from about 0.05 to about 20% by weight, based on the weight of the composition.

7. The composition of claim 1, wherein the oil-soluble polar modified polymer is present in an amount of from about 1% to about 30% by weight, based on the weight of the composition.

8. The composition of claim 5, wherein the oil-soluble polar modified polymer is present in an amount of from about 1% to about 30% by weight, based on the weight of the composition.

9. The composition of claim 6, wherein the oil-soluble polar modified polymer is present in an amount of from about 1% to about 30% by weight, based on the weight of the composition.

10. The composition of claim 1, wherein the oil-soluble polar modified polymer is a polypropylene and/or polyethylene homopolymer or copolymer modified with maleic anhydride units.

11. The composition of claim 1, wherein water is present in an amount of from about 5 to about 50% by weight, based on the weight of the composition.

12. The composition of claim 1, wherein the emulsion is in the form of a foundation.

13. The composition of claim 1, wherein the hyperbranched polyol has a hydroxyl number between 100 and 200.

14. The composition of claim 1, wherein the hyperbranched polyol has a viscosity between 3,000 and 6,000 cps at 90° F.

15. The composition of claim 1, wherein the gelling agent is a cellulosic gelling agent.

16. The composition of claim 15, wherein the cellulosic gelling agent is selected from the group consisting of hydroxyethylcellulose, hydroxypropylcellulose, methylcellulose, ethylhydroxyethylcellulose, carboxymethylcellulose and cellulose.

17. The composition of claim 1, wherein the cellulosic gelling agent is present in an amount of from about 0.1% to about 10.0% by weight of the total weight of the composition.

18. The composition of claim 1, further comprising at least one colorant.

19. A method of making-up skin, wherein the method comprises applying onto the skin in an amount sufficient to make up the skin a composition comprising:
   a water-insoluble, half acid and half amide crosslinked reaction product comprising (1) at least one oil-soluble polar modified polymer comprising at least one C2-C4 monomer and modified with at least one hydrophilic unit, and having a weight-average molecular weight of less than or equal to 25,000 g/mol and a melting point above 75° C. and (2) at least one polyamine, wherein the reaction product forms a matrix capable of entrapping water;
   at least one gelling agent;
   at least one hyperbranched polyol; and
   water,
   wherein the composition is in the form of an emulsion and wherein water is entrapped within the matrix.

20. The composition of claim 1, wherein the weight-average molecular weight of the oil-soluble polar modified polymer is from 1,000 g/mol to 22,000 g/mol.

21. The composition of claim 1, wherein the melting point of the oil-soluble polar modified polymer is between 90° C. and 160° C.

22. The composition of claim 1, wherein the oil-soluble polar modified polymer has from about 0.5% to about 10% hydrophilic units by weight with respect to the weight of the oil soluble polar modified polymer.

23. The composition of claim 1, wherein the oil-soluble polar modified polymer has from about 1% to about 8% hydrophilic units by weight with respect to the weight of the oil soluble polar modified polymer.

24. The composition of claim 22, wherein the oil-soluble polar modified polymer has from about 0.5% to about 10% maleic anhydride units by weight with respect to the weight of the oil soluble polar modified polymer.

25. The composition of claim 23, wherein the oil-soluble polar modified polymer has from about 1% to about 8% maleic anhydride units by weight with respect to the weight of the oil soluble polar modified polymer.

26. The composition of claim 1, wherein the polyamine is polyethyleneimine.

27. The composition of claim 1, wherein the polyamine is in the form of a branched polymer or a dendrimer.

28. The method of claim 19, wherein the polyamine is in the form of a branched polymer or a dendrimer.

* * * * *

UNITED STATES PATENT AND TRADEMARK OFFICE
CERTIFICATE OF CORRECTION

PATENT NO. : 8,540,973 B2  
APPLICATION NO. : 12/825730  
DATED : September 24, 2013  
INVENTOR(S) : Hy S. Bui et al.

Page 1 of 1

It is certified that error appears in the above-identified patent and that said Letters Patent is hereby corrected as shown below:

In the Claims

Column 17, line 40, "75° C." should read --75° C--.

Column 18, line 42, "75° C." should read --75° C--;
    line 54, "90° C." should read --90° C--.

Signed and Sealed this
Fourth Day of February, 2014

Michelle K. Lee
*Deputy Director of the United States Patent and Trademark Office*